(12) United States Patent
Yoon et al.

(10) Patent No.: US 7,947,497 B2
(45) Date of Patent: May 24, 2011

(54) METHODS FOR VITRIFICATION OF HUMAN OOCYTES

(75) Inventors: Tae Ki Yoon, Seoul (KR); Dong Ryul Lee, Seoul (KR); Hyung Min Chung, Namyangju-si (KR); Kwang Yul Cha, Seoul (KR)

(73) Assignees: Chabio&Diostech Co. Ltd., Yongin (KR); College of Medicine Pochon Cha University Industry-Academic Cooperation Foundation, Pochon-siu (KR)

( * ) Notice: Subject to any disclaimer, the term of this patent is extended or adjusted under 35 U.S.C. 154(b) by 0 days.

(21) Appl. No.: 10/581,260

(22) PCT Filed: Apr. 17, 2006

(86) PCT No.: PCT/KR2006/001409
§ 371 (c)(1),
(2), (4) Date: Jul. 7, 2006

(87) PCT Pub. No.: WO2007/119892
PCT Pub. Date: Oct. 25, 2007

(65) Prior Publication Data
US 2009/0081782 A1 Mar. 26, 2009

(51) Int. Cl.
*C12N 5/00* (2006.01)
*C12N 5/02* (2006.01)
*C12N 5/071* (2006.01)
*C12N 15/00* (2006.01)
*A01N 1/00* (2006.01)
*A01N 1/02* (2006.01)

(52) U.S. Cl. .......... 435/374; 435/1.3; 435/366; 435/455

(58) Field of Classification Search .................... 435/374
See application file for complete search history.

(56) References Cited

U.S. PATENT DOCUMENTS
5,976,567 A * 11/1999 Wheeler et al. ............... 424/450

OTHER PUBLICATIONS

Christopher Chen, "Pregnancy After Human Oocyte Cryopreservation", The Lancet, Apr. 19, 1986, pp. 884-886.

R. Fabbri et al, "Human Oocyte Cryopreservation: New Perspectives Regarding Oocyte Survival", Human Reproduction vol. 16, No. 3, pp. 411-416, 2001.
James J. Stachecki et al, "Detrimental Effects of Sodium during Mouse Oocyte Cryopreservation", Biology of Reproduction 59, pp. 395-400 (1998).
Carlos J. Quintans et al, "Birth of Two Babies Using Oocytes That Were Cryopreserved in a Choline-Based Freezing Medium", Human Reproduction vol. 17, No. 12, pp. 3149-3152, 2002.
Jeffrey Boldt et al, "Human Oocyte Cryopreservation as an Adjunct to IVF-Embryo Transfer Cycles", Human Reproduction vol. 18, No. 6, pp. 1250-1255, 2003.
Seung W. Hong, M.S. et al, "Improved Human Oocyte Development After Vitrification: A Comparison of Thawing Methods", Fertility and Sterility vol. 72, No. 1, Jul. 1999, pp. 142-146.
Hyung M. Chung, Ph.D. et al, "In Vitro Blastocyst Formation of Human Oocytes Obtained from Unstimulated and Stimulated Cycles After Vitrification at Various Maturational Stages", Fertility and Sterility vol. 73, No. 3, Mar. 2000, pp. 545-551.
Tae K. Yoon, M.D. et al, "Pregnany and Delivery of Healthy Infants Developed From Vitrified Oocytes in a Stimulated In Vitro Fertilization-Embryo Transfer Program", Fertility and Sterility vol. 74, No. 1, Jul. 2000, pp. 180-181.
Tae Ki Yoon, M. D. et al, "Live Births After Vitrification of Oocytes in a Stimulated In Vitro Fertilization-Embryo Transfer Program", Fertility and Sterility vol. 79, No. 6, Jun. 2003, pp. 1323-1326.
A. Martino et al, "Development Into Blastocysts of Bovine Oocytes Cryopreserved by Ultra-Rapid Cooling", Biology of Reproduction 54, pp. 1059-1069 (1996).
K. Cha et al., "Improved Clinical Outcomes Were Obtained From Vitrified Oocytes Using Gold Grid and Slush-Liquid Nitrogen After Failing the Fresh IVF-ET Program", Fertility and Sterility vol. 84 Supplement 1, Sep. 2005, pp. S351-S352.
H. G. Kim et al., "Effect of slush $LN_2$ and sodium-depleted medium on the survival of the mouse and human oocytes after vitrification", Fertility and Sterility vol, 82 Supplement 2, Sep. 2004, p. S25.
T. K. Yoon et al., "Successful Clinical Application of Oocyte Vitrification Using Gold Grid and Slush-Liquid Nitrogen", Fertility and Sterility vol. 84 Supplement 1, Sep. 2005, p. S476.

* cited by examiner

*Primary Examiner* — Valarie Bertoglio
(74) *Attorney, Agent, or Firm* — Rothwell, Figg, Ernst & Manbeck, P.C.

(57) ABSTRACT

Provided are methods for the vitrification of human oocytes, which comprises: (a) placing human oocytes on a transfer instrument; and (b) placing the transfer instrument and the human oocytes directly into a slushed nitrogen ($N_2$ slush), wherein the human oocytes are directly exposed to the $N_2$ slush thereby undergoing vitrification, and wherein the human oocytes are able to live for a period of time after the human oocytes are devitrified.

4 Claims, 3 Drawing Sheets

METHODS FOR VITRIFICATION OF HUMAN OOCYTES

CROSS REFERENCE TO RELATED APPLICATION

This application is a 35 USC §371 National Phase Entry Application from PCT/KR2006/001409, filed Apr. 17, 2006, and designating the United States.

TECHNICAL FIELD

The present invention relates to a method for the vitrification of human oocytes, such that the human oocytes remain viable after it is thawed. And, the present invention also relates to human oocytes which has undergone vitrification produced by the method; a method for the vitrification and devitrification of human oocytes; and a method for the vitrification and storage of human oocytes.

BACKGROUND ART

Since the first pregnancy from frozen human mature oocytes (Chen, Pregnancy after human oocyte cryopreservation. Lancet 1986; i: 884-6), various studies have been performed to develop methods for cryopreservation of human oocytes. Surplus mature oocytes from the patients who underwent in vitro fertilization-embryo transfer (IVF-ET) were stored for future use by slow cooling or vitrification methods in a lot of clinics. When the patients failed to become pregnant in their fresh IVF-ET cycles, stored oocytes were recovered and provided for an additional IVF-ET.

Although cryopreservation of human oocytes has performed successfully and also has been introduced widely into human assisted reproductive technology (ART), the clinical outcomes are still limited, because of low pregnancy and implantation rates due to poor viability of thawed oocytes. To improve the viability and quality of oocytes after thawing, modified protocols in slow cooling have been suggested to improve survival rates, e.g., changes involving increase in sucrose concentration (Fabbri et al., Human oocyte cryopreservation: new perspectives regarding oocyte survival. Hum Reprod 2001; 16:411-6) or the replacement of sodium with choline in the freezing media (Stachecki et al., Detrimental effect of sodium during mouse oocyte cryopreservation. Hum Reprod 1998a; 59: 395-4001998; Quintans et al., Birth of two babies using oocytes that were cryopreserved in a choline-based freezing medium. Hum Reprod 2002; 17: 3149-52; Boldt et al, Human oocyte cryopreservation as an adjunct to IVF-embryo transfer cycles. Hum Reprod 2003; 18: 1250-5).

The present inventors have developed a vitrification method for the cryopreservation of human oocytes and got quite a good clinical result (Hong et al., Improved human oocyte development after vitrification: a comparison of thawing methods. Fertil Steril 1999; 72: 142-6; Chung et al., In vitro blastocyst formation of human oocytes obtained from unstimulated and stimulated cycles after vitrification at various maturational stages. Fertil Steril 2000; 73: 545-51; Yoon et al., Pregnancy and delivery of healthy infants developed from vitrified oocytes in a stimulated in vitro fertilization-embryo transfer program. Fertil Steril 2000; 74: 180-1; Yoon et al., Live birth after vitrification of oocytes in a stimulated in vitro fertilization-embryo transfer program. Fertil Steril 2003; 79: 1323-6).

Recently, Martino, et al (Biology of Reproduction, vol. 54, pp 1059-1069, 1996) discloses a method for cryopreserving bovine oocytes in which oocytes were placed in a cryopreservative medium, and placed either in straws or on electron microscope grids. The straws were plunged into liquid nitrogen and the grids were either plunged into liquid nitrogen or nitrogen slush. Martino, et al. report that cooling rates achieved with grids were much higher than with straws. To test whether the use of even faster cooling rates would improve survival, nitrogen slush was compared to liquid nitrogen for freezing oocytes on grids. Survival rates based on morphology, cleavage and blastocyst formation were higher for bovine oocytes frozen in liquid nitrogen compared to those frozen in nitrogen slush.

DISCLOSURE OF INVENTION

Technical Problem

While optimizing our vitrification methods for human oocytes, the present inventors surprisingly found that when a slushed nitrogen ($SN_2$) was introduced instead of liquid nitrogen ($LN_2$), the survival rate of vitrified human oocytes was significantly increased and the apoptosis after thawing was significantly decreased. These findings differ from the Martino, et al.'s teaching that survival rates based on morphology, cleavage and blastocyst formation were higher for bovine oocytes frozen in liquid nitrogen compared to those frozen in nitrogen slush.

Therefore, it is an object of the present invention to provide a method for the vitrification of human oocytes.

Further, it is an object of the present invention to provide human oocytes which has undergone vitrification produced by the method.

Further, it is an object of the present invention to provide a method for the vitrification and devitrification of human oocytes and/or a method for the vitrification and storage of human oocytes.

Technical Solution

According to an aspect of the present invention, there is provided a method for the vitrification of human oocytes, which comprises: (a) placing human oocytes on a transfer instrument; (b) placing the transfer instrument and the human oocytes directly into a slushed nitrogen ($N_2$ slush), wherein the human oocytes are directly exposed to the $N_2$ slush thereby undergoing vitrification, and wherein the human oocytes are able to live for a period of time after the human oocytes are devitrified.

According to another aspect of the present invention, there is provided human oocytes which has undergone vitrification produced by the method.

According to still another aspect of the present invention, there is provided a method for the vitrification and devitrification of human oocytes, which comprises: (a) placing human oocytes on a transfer instrument; (b) placing the transfer instrument and the human oocytes directly into a slushed nitrogen ($N_2$ slush), wherein the human oocytes are directly exposed to the $N_2$ slush thereby undergoing vitrification, and wherein the human oocytes are able to live for a period of time after the human oocytes are devitrified; and (c) devitrifying the human oocytes which have undergone vitrification.

According to still another aspect of the present invention, there is provided a method for the vitrification and storage of human oocytes, which comprises: (a) placing human oocytes on a transfer instrument; (b) placing the transfer instrument and the human oocytes directly into a slushed nitrogen ($N_2$ slush), wherein the human oocytes are directly exposed to the $N_2$ slush thereby undergoing vitrification, and wherein the human oocytes are able to live for a period of time after the human oocytes are devitrified; (c) transferring the human oocytes which have undergone vitrification into a storage container, the storage container containing a freezing material; and (d) storing the storage container containing the human oocytes which have undergone vitrification until the human oocytes are ready to devitrified.

BRIEF DESCRIPTION OF THE DRAWINGS

The above and other features and advantages of the present invention will become more apparent by describing in detail exemplary embodiments thereof with reference to the attached drawings in which:

FIG. 4. is survival, fertilization and cleavage rates after warming of human oocytes. FIG. 5. is pregnancy and implantation rates after embryo transfer. *P<0.05.

MODE FOR THE INVENTION

Figure 1:
FIG. 1 is photographs of nitrogen slush ($SN_2$, A-C). (A) Gas bubbles were formed when grid was immersed into $LN_2$ (B) $SN_2$ was formed in chamber when negative pressure was applied. (C) No bubble was formed in $SN_2$.

In the present application, the following terms are used throughout and are defined for the purposes of this application as follows:

By "cryopreservation" it is meant the storage of biological materials, including human oocytes, at below the freezing point of water such that the material does not decompose.

By "vitrification" it is meant a process of cooling biological material, employing cryoprotectants (chemicals that protect water from freezing) to inhibit the formation of ice in the cooling process, to a temperature about −100° C. or lower, such that the solution containing the biological material reaches its glass transition temperature, that is the molecules cease to move relative to each other. It is recognized in the art that ice formation is damaging to biological material, in that it forces the material into shrinking pockets of residual unfrozen solution. As cooling continues, more than eighty percent of tissue volume can become converted to ice, and cells crushed beyond recovery. During vitrification, liquid water molecules maintain their natural random arrangements during deep cooling. There is no disturbance of other chemicals or cell components. Successful vitrification techniques make use of supercooling that is cooling below the freezing point of the cryoprotection solution without freezing. Cryoprotectants are typically toxic to cells at high concentrations. Rapid freezing is believed to work by decreasing the concentration of cryoprotectant necessary to protect against ice crystal formation, thereby preserving the tissue at non-toxic concentrations of cryoprotectants.

By "directly exposed" it is meant that human oocytes are "directly exposed" to a freezing material if the majority of the surface of the human oocytes, or the medium, solution or material in which the human oocytes resides, is allowed to come into direct contact with the freezing material.

By "viable" it is meant human oocytes which are able to live and develop normally for a period of time.

By "transfer instrument" it is meant an instrument used to manipulate human oocytes into a freezing material which is structured in such a fashion that it encircles and/or holds the human oocytes, and/or the medium, solution or material containing the human oocytes, in place during the vitrification process and/or allows ease of manipulation of the human oocytes within the freezing material, and wherein the transfer instrument allows the human oocytes to be directly exposed to the freezing material. The transfer instrument may be any such instrument generally known in the art, including, but not limited to a loop, net with handle, paddle with handle instrument, electron microscopy grids or straws.

According to the method of the present invention, human oocytes are placed directly into a slushed nitrogen, i.e., $N_2$ slush, such that the human oocytes are directly exposed to the $N_2$ slush. Upon exposure to the $N_2$ slush, the human oocytes undergo vitrification. The human oocytes which have undergone vitrification may be stored for a period of time, and then thawed at a later date. The thawed human oocytes remain viable.

$N_2$ slush may be prepared in accordance with known arts, e.g., Biology of Reproduction 54, 1059-1069 (1996) or U.S. Pat. No. 5,715,686. For example, $N_2$ slush may be generated in a rapid-cooling (−210° C.) liquid nitrogen chamber (VitMaster™, IMT, Israel) by applying negative pressure. Since $N_2$ slush has a lower internal temperature without vaporization (see FIG. 1), it could mediate high cooling rates and may increase the survival rate of oocytes after vitrification.

In a preferred embodiment, the human oocytes are placed on a transfer instrument prior to vitrification. The transfer instrument can be any instrument that allows the human oocytes to be transported into a freezing material, while allowing the human oocytes to be directly exposed to the freezing material, allowing the human oocytes to be cooled very quickly, thus allowing the human oocytes to vitrify rather than form ice crystals within the cell, which would in turn ultimately disrupt vital cellular constituents.

The transfer instrument in the present invention encircles and/or holds the human oocytes in place during the vitrification process, so that the human oocytes are not lost during the process. Therefore, the transfer instrument does not just allow the human oocytes to rest upon it, as with flat sheets or microscopy grids, but may actually help keep the human oocytes in place. Preferred transfer instrument of the present invention is a gold grid, one of electron microscopy grids. Further, commercially available gold grids, such as electron microscope gold grid (Gilder, Westchester, Pa.) may be used in the present invention. It has been surprisingly discovered that the use of a gold grid in the present vitrification method provides low-toxicity and extremely high heat conductivity, thereby allowing fast cooling rates, ease of visualization, facile manipulations and a high success rate of viability when the vitrified human oocytes are thawed and cultured.

In a preferred embodiment, the human oocytes are treated with a small amount of a cryoprotectant prior to vitrification. The method of the present invention also allows for a decrease in the time of exposure of the human oocytes to the solution phase of the cryoprotectant used, thus lowering the toxicity of the cryoprotectant to the human oocytes. Cryoprotectants, such as ethylene glycol, polyethylene glycol, dimethylsulfoxide, glycerol, propane diol, sugars, and methyl pentane diol, as well as others well known in the art, can be toxic to sensitive cells such as oocytes when used in large dosages during cryopreservation. Any optional cryoprotectant present in solution phase may be used in the present invention.

The pre-treatment of human oocytes with a cryoprotectant may comprises treating human oocytes with a first phosphate buffered saline supplemented with about 1.5 M of ethylene glycol and 10% (v/v) of fetal bovine serum for about 2.5 minutes and then treating with a second phosphate buffered saline supplemented with about 5.5 M of ethylene glycol, about 1.0 M of sucrose, and about 10% (v/v) of fetal bovine serum for about 20~30 seconds.

The transfer instrument containing the human oocytes is then quickly placed in a freezing material, i.e., a slushed nitrogen ($N_2$ slush), such that the human oocytes are directly exposed to the $N_2$ slush, allowing vitrification of the human oocytes. Preferably, the human oocytes are held within the $N_2$ slush during all manipulations subsequent to vitrification, until the specimen is to be thawed.

In accordance with another aspect of the present invention, there is provided method for the vitrification and devitrification of human oocytes, which comprises: (a) placing human oocytes on a transfer instrument; (b) placing the transfer instrument and the human oocytes directly into $N_2$ slush, wherein the human oocytes are directly exposed to the $N_2$ slush thereby undergoing vitrification, and wherein the human oocytes are able to live for a period of time after the human oocytes are devitrified; and (c) devitrifying the human oocytes which have undergone vitrification.

The devitrifying step may include thawing the human oocytes which have undergone vitrification. Thawing may be performed in accordance with methods in the known arts, e.g., Hong S W et. al., Improved human oocyte development after vitrification: a comparison of thawing methods. Fertil Steril 2000, 73, 545-551. For example, for thawing, the transfer instrument (e.g., gold grid) containing human oocytes may be sequentially transferred to culture mediums of phosphate buffered saline supplemented with about 1.0, about 0.5, about 0.25, about 0.125, and about 0 M of sucrose and 10% (v/v) of fetal bovine serum at intervals of about 2 minutes at 37° C.

The present invention also relates to a method for the vitrification and storage of human oocytes, which comprises: (a) placing human oocytes on a transfer instrument; (b) placing the transfer instrument and the human oocytes directly into $N_2$ slush, wherein the human oocytes are directly exposed to the $N_2$ slush thereby undergoing vitrification, and wherein the human oocytes are able to live for a period of time after the human oocytes are devitrified; (c) transferring the human oocytes which have undergone vitrification into a storage container, the storage container containing a freezing material; and (d) storing the storage container containing the human oocytes which have undergone vitrification until the human oocytes are ready to devitrified.

The storage container contains a freezing material, including, but not limited to, liquid gases such as liquid nitrogen, liquid propane, or liquid helium.

The methods of the present invention can improve the clinical efficacy of human oocyte vitrification and be a valuable tool for human assisted reproduction.

Hereinafter, the present invention will be described more specifically by examples. However, the following examples are provided only for illustrations and thus the present invention is not limited to or by them.

EXAMPLE 1

Vitrification and Thawing

The institutional review board of CHA General Hospital, Seoul, Korea, approved all of the clinical studies and applications in January 2003. All of the participants gave their informed consents.

1. Controlled Ovarian Hyper-stimulation for Standard IVF-ET

Starting on third day of cycle, controlled ovarian hyper-stimulation was done with recombinant FSH or recombinant FSH/human menopause gonadotropin. And, to prevent pre-mature LH surge in the long protocol, GnRH-agonist (Lucrin; Abbott, Seoul, Korea) was used to get pituitary down regulation. In other case, GnRH antagonist Cetrorelix (Cetrotide, Serono) was used after 5-6 days of stimulation. Ovulation was triggered with 250 ☐of recombinant hCG (Ovidrel; Serono) when at least two follicles were over 18 mm in diameter. Transvaginal oocyte retrieval was done 34-36 hours after the hCG administration.

2. Generation of $SN_2$ $N_2$ slush was generated in a rapid-cooling (−210° C.) $LN_2$ chamber (Vit-Master™, IMT, Israel) by applying negative pressure. To make $N_2$ slush, the chamber was filled ¾ with liquid nitrogen and then vacuum pump was switched on. Around 10-20minutes later, temperature in chamber was declined to maximum −210° C. and pressure was also lowered into almost 0 bars. Finally, liquid nitrogen in the chamber was changed into slush state, $N_2$ slush.

3. Vitrification and Thawing of Oocytes

Recovered cumulus-oocytes complex (COC) or fertilization-failed oocytes were briefly incubated for 10 seconds with 80 IU/ml of hyaluronidase to remove excess cumulus cells (CC), and were then pre-equilibrated for 2.5 minutes in 2 mL of Dulbecco's phosphate buffered saline (DPBS, Gibco BRL, Grand Island, N.Y.) supplemented with 1.5 M of ethylene glycol (EG, E-9129; Sigma, St. Louis, Mo.) and 10% (vol/vol) fetal bovine serum (FBS, Gibco BRL, Grand Island, N.Y.) at 37° C. COC or oocytes were then placed for the final equilibration in the same volume of DPBS supplemented with 5.5 M EG, 1.0 M sucrose, and 10 % FBS for 20 seconds.

Two to five COC or oocytes were mounted on an electron microscope gold grid (Gilder, Westchester, Pa.) using a fine glass pipette. And excess cryoprotectant solution was removed with the underlying sterilized papers (Kimwipes, Yuhan-Kimberly, Gunpo, Korea). The gold grids containing oocytes or COC were immediately plunged into either $LN_2$ (Liquid $N_2$) or $SN_2$ ($N_2$ slush). For long-term storage, a cryovial cap and goblet were used for placement of the grid.

For thawing after the storage of 1-17 months, the gold grids were sequentially transferred to culture dishes containing 2 mL of DPBS supplemented with 1.0, 0.5, 0.25, 0.125, or 0 M sucrose and 10% (vol/vol) FBS at intervals of 2.5 minutes at 37° C.

EXAMPLE 2

Assessment of Vitrified Oocytes

Unless otherwise specified, data were expressed as mean±SEM. Clinical outcome from $SN_2$-vitrification was compared with those from conventional $LN_2$-vitrification of Yoon et. al., Fertil Steril (2003) June; 79(6): 1323-1326 performed from October 1997 to December 2002. The Chi-square test and Student's t-test were used for statistical comparison. $P<0.05$ was considered statistically significant.

1. Survival Rate and Apoptosis

The recovered oocytes in Example 1 were monitored their survival based on intact morphology, and CC of GV oocytes were sampled for analysis of apoptosis after incubation for 0 or 3 hours. Total of 545 discarded oocytes from conventional IVF were divided into two groups and vitrified by using either conventional $LN_2$ or $SN_2$. CC were harvested and stored at −80° C. until the use in order to quantify apoptotic cells.

Lysis buffer was added into eppendorf tube containing CC (5 COC/tube) and resuspended for nucleosomes purification using genomic DNA extraction kit (DNeasy™ Tissue kit, Qiagen, Valencia, Calif.). Relative quantity of apoptosis was analyzed by in vitro determination of the cytoplasmic histone-associated DNA fragments by using Cell death Detection ELISA kit (Cat. No. 1 544 675, Roche, Penzberg, Germany). An anti-histone antibody was fixed adsorptively on the bottom of microtiter plate. After blocking non-specific binding sites, samples (5 ▭of genomic DNA) were added. Nucleosomes bind to the immobilized anti-histone antibody. The second antibody (peroxidase labeled anti-DNA antibody) reacts with the DNA region of the nucleosome. After removal of unbound peroxidase conjugate, the amount of peroxidase retained in the immunocomplex was determined photometrically with a substrate so that apoptosis (at 420 nm wave length) could be related to protein content.

Figure 2:
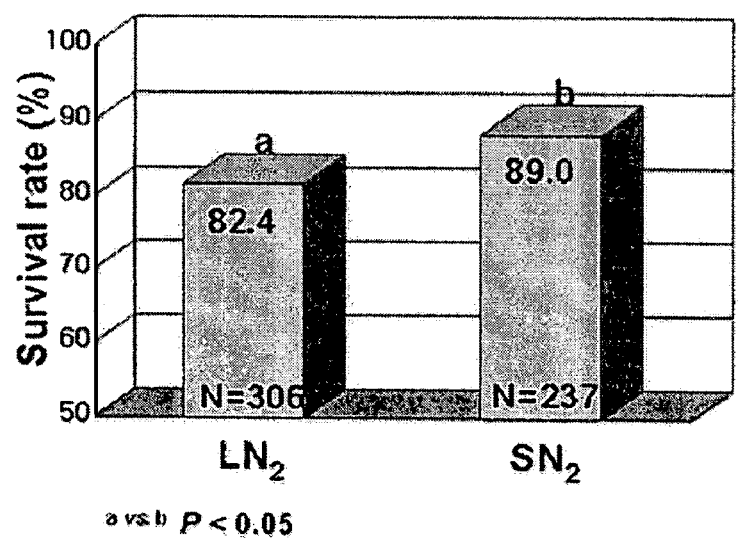
FIG. 2 is survival rate of human fertilization-failed oocytes after vitrification using $LN_2$ or $SN_2$. Different superscripts indicate significant differences (P<0.05).
Figure 3:
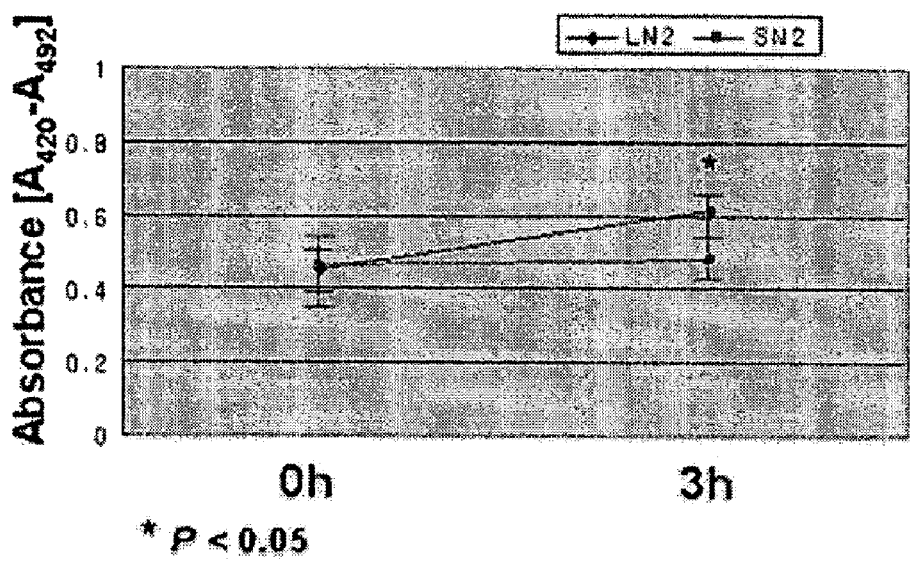
FIG. 3 is the results of quantification of apoptosis in cumulus cells by detecting peroxidase labeled anti-DNA antibody reacted with the DNA region of the nucleosome after vitrification using $LN_2$ or $SN_2$. *P<0.05

As shown in FIG. 2, survival rate with intact morphology was increased in vitrified oocytes using $SN_2$ compared to those using conventional $LN_2$ (89.0% (211/237) vs. 82.4% (252/306), P<0.05). And the effect of the cooling speed on the apoptosis during vitrification was analyzed in CC recovered from vitrified/thawed COC using $LN_2$ or $SN_2$. Just after warming, there was no difference in the mean OD value of nucleosome bound to the immobilized anti-histone antibody for detecting relative amount of apoptosis between the two groups (0.4576±0.048 vs. 0.4665±0.060). However, after 3 hours of warming, mean OD value in CC from $LN_2$-vitrification was 0.6168±0.043, which was significantly higher (P<0.05) than that in CC from $SN_2$-vitrification in which it was 0.4280±0.036 (FIG. 3).

2. Oocyte Freezing for Patients

From December 2003 to August 2005, 76 patients agreed to participate in an oocytes cryopreservation protocol using the $SN_2$-vitrification method for the surplus oocytes while they were undergoing IVF cycles. After failing the fresh-IVF cycles, 28 patients (30 cycles) returned for ET using vitrified-warmed oocytes. The mean (±SD) age and duration of infertility for the patients were 33.7±4.6 years and 4.5±2.8 years, respectively. Reasons for the IVF-ET were as follows: tubal factors (n=10), male factors (n=8), unexplained cause (n=4), ovum donation (n=2), polycystic ovarian syndrome (n=3) and endometriosis (n=1). The average number of IVF attempts was 2.0±1.7.

In our center, patients with more than 15 oocytes retrieved are given the option to freeze their supernumerary oocytes for next use. For transfer of embryos derived from cryopreserved oocytes, we performed warming and intracytoplasmic sperm injection (ICSI) on the day of ovulation in the natural cycles or after reaching adequate endometrial thickness using hormone replacement with E2 valerate (Progynova; Schering, Berlin, Germany). Oocytes were stored for 1-17 months before thawing; the mean interval between the fresh and vitrified cycles was 4.3 months.

3. Fertilization, Embryo Culture, and Embryo Transfer

After being washed four to six times, CC were removed by mechanical pipetting and then transferred into the Preimplantation-1 (P-1) medium (Irvine Scientific, Irvine, Calif.) with 10% synthetic serum substitute (SSS, Irvine Scientific). Oocytes were defined as morphologically survived if they possessed an intact zona pellucida, plasma membrane, and a refractive cytoplasm. ICSI was performed 3-6 hours after the incubation of oocytes. The number of pronuclei in the cytoplasm was counted to verify normal fertilization of vitrified/warned oocytes at 16-19 hours after ICSI. The embryos from 2PN zygotes were cultured in the P-1 medium with 10% SSS. Embryos were transferred to the uterus 3 days after the ICSI procedure. E2 valerate (6 mg/day, Schering) and progesterone supplementation (50 mg/day, Samil Pham. Inc., Seoul, Korea) was started on the day of oocyte warming (Day 0). Transfers were performed on the Day 3. Endometrium thickness was checked before starting progesterone administration, and the cycle was suspended if the lining was thinner than 7 mm or thicker than 12 mm. Pregnancy was identified by the serum β-hCG level, checked 12 days after ET. On diagnosing the pregnancy, a maternal blood dual test and amniocentesis to exclude fetal anomalies were performed.

Figure 4:
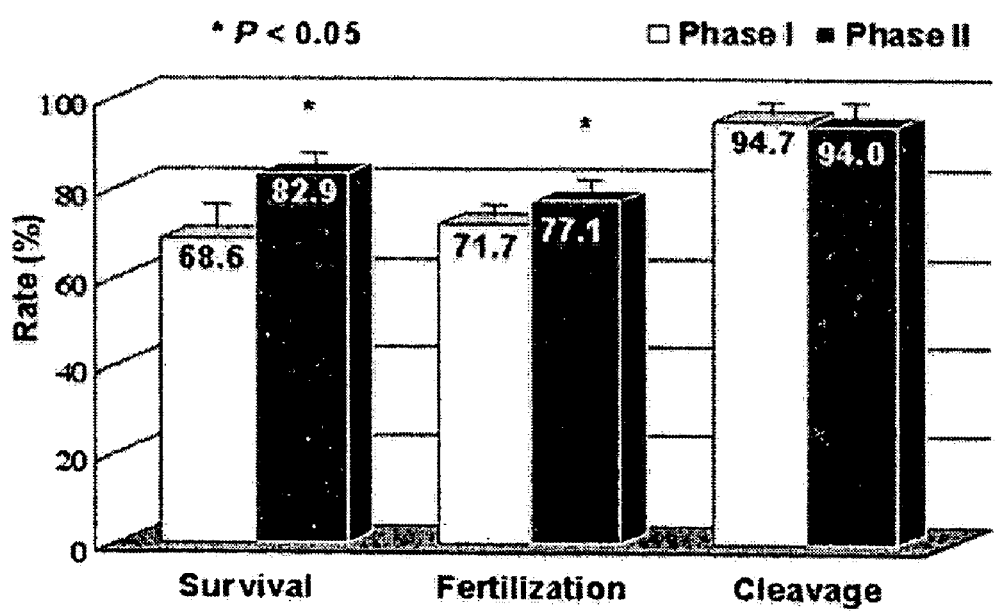
FIG. 4 and FIG. 5 are clinical outcomes of vitrified human mature oocytes from stimulated cycles according to cooling method using $LN_2$ or $SN_2$. Phase I was from October 1997 to December 2002 when vitrification using conventional $LN_2$ was performed for clinical oocytes cryopreservation. Phase II was from November 2003 to August 2005 when vitrification using $SN_2$ was performed for clinical oocytes cryopreservation.
Figure 5:
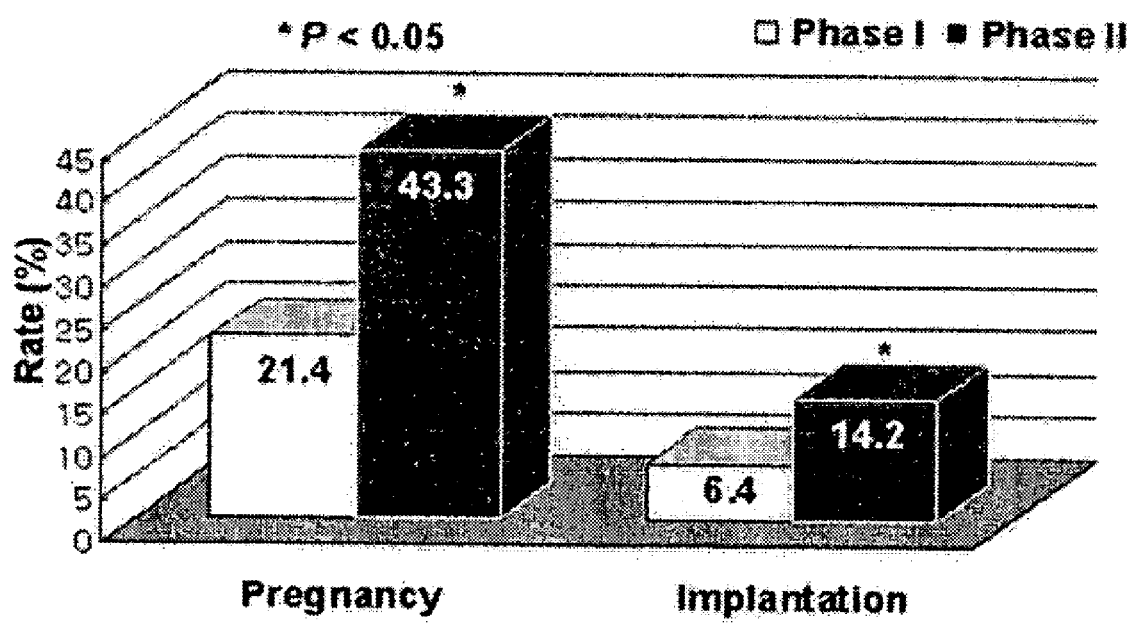

Of the 784 COC (26.1±2.5) retrieved from 28 patients, 358 oocytes were used for fresh IVF-ET cycles, and the remaining 426 COC were cryopreserved according to the same methods in Example 1. Two patients of those were received two times of embryo transfer. A morphological survival rate of oocytes was 82.9±2.9% (302/364). Of those, 72.2% (218/302) were metaphase II oocytes suitable for ICSI procedure. Fertilization rate of these vitrified/warmed oocytes was 77.1±3.5% (168/218), and cleavage rate on day 2 was 94.0% (158/168) (FIG. 4). The average number of embryos transferred was 4.0±0.2. All patients who hope the using of frozen oocytes entered their all ET procedures without cancellation. A total of 120 cleaving embryos from vitrified oocytes were transferred to the 30 cycles of 28 patients, and 13 patients achieved clinical pregnancies. The pregnancy per ET and implantation rates of vitrified IVF-ET were 43.3% (13/30) and 14.2% (17/120), respectively (FIG. 5). Two pregnancies were miscarried at 8-weeks and at 9-weeks (one abortus was 88+XXYY of chromosome, and the other was normal 44+XY). Four pregnancies were delivered 5 normal babies (three singletons (male/male/female) and one twin (male/male)) and remained 7 pregnancies are well ongoing.

Out of 11 patients of this study were not undertaken the ET in their fresh cycles due to several reasons (2 patients were failed fertilization; 5 were on the risk of OHSS; 2 were non-synchronization cycle with ovum donor; 2 were on husband's personal problem). In these patients, pregnancy and implantation rates were much higher in patients without ET on fresh cycle than those with ET (72.7% (8/11), 22.2% (12/54) vs. 29.4% (5/17), 7.6% (5/66), P<0.05).

The invention claimed is:

1. A method for the vitrification of human oocytes, which comprises:
   (a) placing human oocytes on a gold grid; and
   (b) placing the gold grid and the human oocytes directly into a slushed nitrogen ($N_2$ slush), wherein the human oocytes are directly exposed to the $N_2$ slush thereby undergoing vitrification, and wherein implantation or pregnancy rate of human oocytes after devitrification and in vitro fertilization is higher than implantation or pregnancy rate of human oocytes vitrified on a gold grid using liquid nitrogen.

2. The method according to claim 1, wherein the step (a) further comprises treating the human oocytes with a cryoprotectant prior to vitrification.

3. A method for the vitrification and devitrification of human oocytes, which comprises:
   (a) placing human oocytes on a gold grid;
   (b) placing the gold grid and the human oocytes directly into $N_2$ slush, wherein the human oocytes are directly exposed to the $N_2$ slush thereby undergoing vitrification, and wherein the human oocytes are able to live for a period of time after the human oocytes are devitrified; and
   (c) devitrifying the human oocytes which have undergone vitrification, wherein implantation or pregnancy rate of human oocytes after in vitro fertilization is higher than implantation or pregnancy rate of human oocytes vitrified on a gold grid using liquid nitrogen.

4. A method for the vitrification and storage of human oocytes, which comprises:
   (a) placing human oocytes on a gold grid;
   (b) placing the gold grid and the human oocytes directly into $N_2$ slush, wherein the human oocytes are directly exposed to the $N_2$ slush thereby undergoing vitrification, and wherein the human oocytes are able to live for a period of time after the human oocytes are devitrified;
   (c) transferring the human oocytes which have undergone vitrification into a storage container, the storage container containing a freezing material; and
   (d) storing the storage container containing the human oocytes which have undergone vitrification until the human oocytes are ready to devitrified,
   wherein implantation or pregnancy rate of human oocytes after devitrification and in vitro fertilization is higher than implantation or pregnancy rate of human oocytes vitrified on a gold grid using liquid nitrogen.

* * * * *